(12) United States Patent
Kimura et al.

(10) Patent No.: US 9,101,588 B2
(45) Date of Patent: Aug. 11, 2015

(54) COMPOSITION FOR LOWERING BLOOD URIC ACID LEVEL

(75) Inventors: Fuminori Kimura, Toshima-ku (JP); Hideaki Kitajima, Toshima-ku (JP); Takao Tanaka, Toshima-ku (JP); Toru Nishikawa, Toshima-ku (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 220 days.

(21) Appl. No.: 13/496,778

(22) PCT Filed: Sep. 10, 2010

(86) PCT No.: PCT/JP2010/065627
§ 371 (c)(1), (2), (4) Date: Mar. 16, 2012

(87) PCT Pub. No.: WO2011/034006
PCT Pub. Date: Mar. 24, 2011

(65) Prior Publication Data
US 2012/0190886 A1  Jul. 26, 2012

(30) Foreign Application Priority Data
Sep. 17, 2009 (JP) ................. 2009-215092

(51) Int. Cl.
C07C 309/00 (2006.01)
A01N 33/00 (2006.01)
A61K 31/13 (2006.01)
A61K 31/16 (2006.01)
A61K 31/185 (2006.01)

(52) U.S. Cl.
CPC .................... *A61K 31/185* (2013.01)

(58) Field of Classification Search
None
See application file for complete search history.

(56) References Cited

FOREIGN PATENT DOCUMENTS

JP  2006-213607 A  8/2006

OTHER PUBLICATIONS

Goodman and Gilman's The Pharmacological Basis of Therapeutics (Tenth Edition (2001), McGraw Hill, Chapter I, pp. 3-29.*
International Preliminary Report on Patentabiity dated Apr. 19, 2012 for corresponding PCT/JP2010/065627.
Himeno, A., et al., "Taurine and Experimental Hypertension", Nutrition, Metabolism and Cardiovascular Diseases, [Proc. Symp.], Meeting Date 1983, 1984, p. 53-58.
Murakami, S., et al., "Effect of Taurine on Cholesterol Metabolism in Hamsters: Up-Regulation of Low Density Lipoprotein (LDL) Receptor by Taurine", Life Sciences, vol. 70, 2002, p. 2355-2366.
Yokogoshi, H., et al., "Dietary Taurine Enhances Cholesterol Degradation and Reduces Serum and Liver Cholesterol Concentrations in Rats Fed a High-Cholesterol Diet", The Journal of Nutrition, vol. 129, 1999, p. 1705-1712.
Murakami, S., et al., "Improvement in Cholesterol Metabolism in Mice Given Chronic Treatment of Taurine and Fed a High-Fat Diet", Life Sciences, vol. 64, No. 1, 1999, p. 83-91.
Oda, H., et al., "Mechanism of Inducing CYP7A1 Gene Expression by Taurine", Reports of the Research Committee of Essential Amino Acids, (Japan), No. 167, 2003, p. 13-16.
Yianjian et al., "Effects of Taurine on Oxidative—Antioxidative Status of Renal Tissue in Diabetic Rats", Journal of Radioimmunology, 17(4):245-247 (2004).

* cited by examiner

*Primary Examiner* — Clinton Brooks
(74) *Attorney, Agent, or Firm* — Sughrue Mion, PLLC

(57) ABSTRACT

A composition for lowering a blood uric acid level is characterized by comprising taurine as an active ingredient.

3 Claims, 4 Drawing Sheets

COMPOSITION FOR LOWERING BLOOD URIC ACID LEVEL

TECHNICAL FIELD

The present invention relates to a composition for lowering a blood uric acid level, the composition comprising taurine as an active ingredient.

BACKGROUND ART

Japanese diet today has been Westernized, and high-fat and high-energy diets tend to be preferred. As a result, unhealthy conditions such as obesity may be incurred. In addition, with alcohol drinking, stresses, or the like serving as a trigger, increase in the uric acid level in a body has been incurred.

Normally, in a healthy condition, much of uric acid is excreted from the body together with urine, sweat, feces, or the like. Meanwhile, if uric acid is excessively synthesized by the influence of the above-described diet and living environment but is not excreted properly, the amount of uric acid in the blood becomes excessive. Such a state of exceeding the saturation solubility (7.0 mg/dL) of uric acid in the blood is hyperuricemia.

In hyperuricemia in which a high blood uric acid level is continued, sodium urate crystals start to precipitate in body tissues. Since the crystals are likely to form at a part where the body temperature is low, the crystals are often deposited in legs and earlobes. Uric acid crystals precipitate in the base of a big toe or the joint of a knee where the crystal deposition is most likely to occur. This may cause inflammation with acute pain (gouty attack). Meanwhile, if a stone is formed in the renal tubule, this may cause a kidney disorder.

Taurine (aminoethylsulfonic acid) is a sulfur-containing amino acid having a quite simple chemical structure with a molecular weight of 125.15. The pharmacological action is known to cover a wide range including the central nervous system, the circulatory system, and the liver/gallbladder system. Particularly, it has been revealed that taurine has a serum cholesterol-lowering action. The main mechanism of the action is thought to be the action of promoting cholesterol catabolism and excretion from the liver (see Non Patent Literatures 1 to 4). Meanwhile, taurine-containing preparations have been sold for a long period in the fields of prescription drugs and also nonprescription drugs and quasi drugs. In Japan, 50 years are about to elapse after the first taurine-containing preparation was sold. Thus, the actual performance of taurine itself is sufficient. It can be said that taurine is one of quite highly safe components.

CITATION LIST

Non Patent Literatures

[NPL 1] Murakami, S., Kondo, Y., Toda, Y., Kitajima, H., Kameo, K., Sakono, M. and Fukuda, N: Effect of taurine on cholesterol metabolism in hamsters: Up-regulation of low density lipoprotein (LDL) receptor by taurine, Life Sci. 70: 2355-2366, 2002.

[NPL2] Yokogoshi, H., Mochizuki, H., Nanami, K., Hida, Y., Miyachi, F. and Oda, H: Dietary taurine enhances cholesterol degradation and reduces serum and liver cholesterol concentrations in rats fed a high-cholesterol diet, J. Nutr. 129: 1705-1712, 1999.

[NPL 3] Murakami, S., Kondo Y. and Tomisawa, K: Improvement in cholesterol metabolism in mice given chronic treatment of taurine and fed a high-fat diet, Life Sci. 64: 83-91, 1999.

[NPL 4] Oda Hiroaki, Arakawa Shingo, Iwata Takeyuki, Nishimura Naomichi, and Yokogoshi Hidehiko: Mechanism of inducing CYP7A1 gene expression by taurine: Reports of the Research Committee of Essential Amino Acids (Japan) 167, 13-16, 2003.

SUMMARY OF INVENTION

Technical Problem

The causes of hyperuricemia and gout are excessive production and decreased excretion of uric acid as described above. At the time of gouty attack, the inflammation is suppressed by administering a nonsteroidal anti-inflammatory analgesic. Further, in order to lower the uric acid level, a lifestyle such as diet is to be improved; besides, in a case where the uric acid level exceeds 9.0 mg/dL, a treatment for lowering the uric acid level is performed by administering an oral drug.

The drug for lowering the uric acid level includes a uric acid-production inhibitor and a uric acid-excretion promoter. When these drugs are taken, it is necessary to take enough water so as to increase a urine volume, and to use baking soda and a urinary alkalinizing agent in combination so as to maintain the alkalinity of the urine so that the pH of urine can be kept between 6.0 and 6.5.

Further, whichever of the drugs is used, the uric acid level has to be checked regularly to control the uric acid level continuously. The treatment is continued for life in many cases. If checking the uric acid level is forgotten in using such drugs, the uric acid level is lowered more than necessary, or side effects such as kidney stone are caused by the drugs in some cases. For this reason, drugs taken continuously in an extended period of time are demanded to be effective as well as highly safe.

Accordingly, an object of the present invention is to provide a composition for suppressing increase in the blood uric acid level which would otherwise cause hyperuricemia and gout, the composition being safe and highly effective even after dosing in an extended period of time.

Solution to Problem

To achieve the above-described object, the present inventors have earnestly studied. As a result, the inventors have found out taurine has an action of lowering a blood uric acid level. This discovery has led to the completion of the present invention.

An aspect according to the present invention is a composition for lowering a blood uric acid level, the composition characterized by comprising taurine as an active ingredient.

A preferable aspect of the present invention is the composition which is anyone of preventive and therapeutic agents for hyperuricemia.

Another preferable aspect of the present invention is the composition which is any one of preventive and therapeutic agents for gout.

Another preferable aspect of the present invention is the composition which is an agent for internal administration.

Advantageous Effects of Invention

The present invention makes it possible to provide a composition for lowering a blood uric acid level, the composition comprising taurine as an active ingredient, and being safe even after administration in an extended period of time.

DESCRIPTION OF EMBODIMENT

Figure 1:
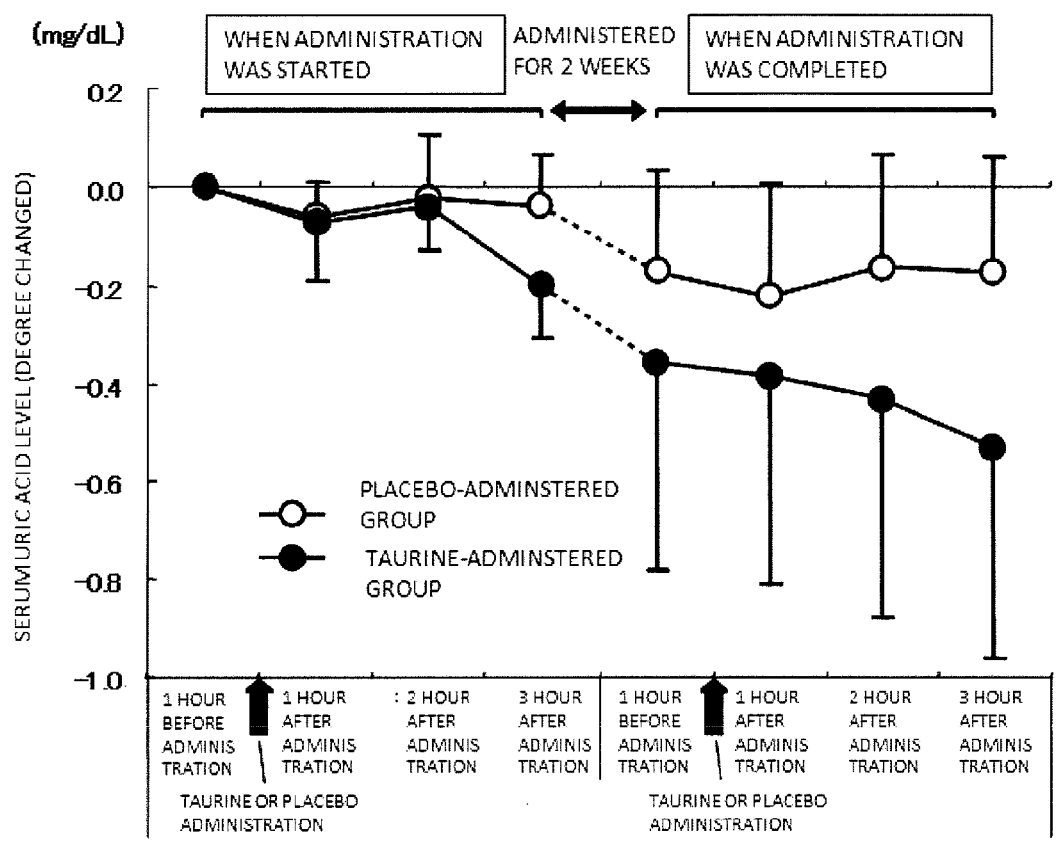
FIG. 1 is a graph illustrating changes in the serum uric acid level of a taurine-administered group and a placebo-administered group.

The present invention provides a composition for lowering a blood uric acid level, the composition characterized by comprising taurine as an active ingredient.

The composition of the present invention may be in the form of a pharmaceutical composition, a food, a drink, or a reagent used for a research purpose (for example, in vivo experiment).

The composition of the present invention has an action of lowering a blood uric acid level. Accordingly, the composition of the present invention can be suitably used as a pharmaceutical composition administered for preventing or treating diseases caused by increase in the blood uric acid level such as, for example, hyperuricemia and gout, and as a food and a drink routinely taken to lower the blood uric acid level.

The composition of the present invention can be formulated by known formulation methods in pharmaceutics. The composition of the present invention can be used orally or parenterally in the form of, for example, a tablet, a granule, a powder, a capsule, a pill, a fine granule, a film coating agent, a pellet, a troche, a sublingual tablet, a masticatory, a buccal, a liquid, a syrup, a suspension, an elixir, an emulsion, a paste, an aerosol, an injection, a suppository, or the like.

When formulated, these can be combined as appropriate with pharmacologically acceptable carrier, food, or drink, specifically, sterile water, a saline, a vegetable oil, a solvent, a base, an emulsifier, a suspension, a surfactant, a stabilizer, a flavor, an aromatic, an excipient, a vehicle, an antiseptic, a binder, a diluent, an isotonic agent, a filler, a disintegrator, a buffer, a coating agent, a lubricant, a colorant, a sweetener, a viscous agent, a corrigent, a solubilizer, or other additives.

When used as a pharmaceutical composition, the composition of the present invention is preferably provided as an oral preparation such as a solid preparation and a liquid preparation for internal administration.

As the solid preparation for internal administration, the composition of the present invention can be provided, for example, in the form of a tablet, a granule, a powder, a capsule, or the like by granulating taurine and other known additives, or other process.

As the liquid preparation for internal administration, the composition of the present invention can be provided, for example, in the form of a drink preparation or the like by dissolving taurine and other known additives in water.

When the composition of the present invention is used as a pharmaceutical composition, it is possible to blend another or two or more other components effective in preventing or treating diseases caused by increase in the blood uric acid level. Moreover, it is possible to use the composition of the present invention in combination with another pharmaceutical composition effective in preventing or treating diseases caused by increase in the blood uric acid level.

In the pharmaceutical composition of the present invention, for example, besides taurine, citric acid (which has an action of maintaining the weak alkalinity of urine so as to facilitate dissolution of uric acid into the urine), vitamin C (which has an action of promoting uric acid excretion by transferring uric acid accumulated in a joint or the like to the kidney), potassium (which has an action of promoting filtration of uric acid in the kidney), folic acid (which has an action of weakening the activation of a uric acid synthase), or the like may be blended as appropriate, as long as the effects of the present invention are not impaired.

When the composition of the present invention is used as a food or drink, the food and drink may be, for example, a health food, a functional food, a food for specified health use, a nutritional supplementary food, a medical food for the ill, or a food additive. The food and drink of the present invention can be taken as the composition as described above, or can be taken as various foods and drinks. Specific examples of the foods and drinks include: liquid-form foods such as drinks, soups, milk drinks, soft drinks, tea drinks, alcoholic drinks, jelly drinks, and functional drinks; products including oil contents such as edible oils, dressings, mayonnaises, and margarines; carbohydrate-containing foods such as rices, noodles, and breads; processed meat products such as hams and sausages; processed fishery products such as kamabokos, dried fishes, and shiokara; processed vegetable products such as tsukemono; semisolid foods such as jellies and yogurts; fermented foods such as misos and fermented drinks; various confectioneries such as Western-style confectioneries, Japanese-style confectioneries, candies, gums, gummies, cold desserts, and frozen desserts; foods in retort pouches such as curries, thick starchy sauces, and Chinese soups; convenience foods such as instant soups and instant miso soups; microwave foods; and the like. Furthermore, the examples include health foods and drinks prepared in the form of a powder, a granule, a tablet, a capsule, a liquid, a paste or a jelly.

In the present invention, the food and drink can be produced by production techniques known in this technical field. The food and drink may be blended with a component or two or more components effective in lowering a blood uric acid level. Further, the food and drink of the present invention may be multifunctional foods and drinks prepared in combination with another component or another functional food which demonstrate a function other than lowering a blood uric acid level.

In the food and drink of the present invention, for example, besides taurine, citric acid (which has an action of maintaining the weak alkalinity of urine so as to facilitate dissolution of uric acid into the urine), vitamin C (which has an action of promoting uric acid excretion by transferring uric acid accumulated in a joint or the like to the kidney), potassium (which has an action of promoting filtration of uric acid in the kidney), folic acid (which has an action of weakening the activation of a uric acid synthase), or the like may be blended as appropriate, as long as the effects of the present invention are not impaired.

When the composition of the present invention is administered or taken, the amount administered or taken is selected as appropriate in accordance with the age, weight, symptom, health state, the type of the composition (such as drug, food, or drink), and the like. An effective amount of taurine administered in the composition of the present invention is 100 mg to 6000 mg, preferably 500 mg to 4000 mg, and more preferably 2000 mg to 4000 mg for an adult per day. Hence, the present invention also provides a method for lowering a blood uric acid level in a target, the method characterized by comprising administering or taking the composition of the present invention into the target. Moreover, the present invention further provides a method for preventing or treating a disease caused by increase in a blood uric acid level in a target, the method characterized by comprising administering the composition of the present invention to the target.

A product (drug, food, drink, reagent) of the composition of the present invention or a protocol thereof may be labeled to indicate that the use is to lower a blood uric acid level. Herein, the phrase "a product or a protocol is labeled" means that the body of the product, a container or a package therefor, or the like is labeled, or that a protocol, an attached document, an advertisement, other prints, or the like disclosing information on the product is labeled. The label indicating that the use is to lower a blood uric acid level may include information about a mechanism of lowering a blood uric acid level by administering or taking the composition of the present invention. Moreover, the label indicating the use is to lower a blood uric acid level may include information that the use is to prevent or treat diseases caused by increase in the blood uric acid level.

EXAMPLES

Hereinafter, the present invention will be described in more details by way of Examples and Test Examples.

Example 1

| | |
|---|---|
| Taurine | 1000 mg/pack |
| Light anhydrous silicic acid | 10 mg/pack |
| Talc | 10 mg/pack |

Components in the amounts listed above were mixed together, and then subjected to wet granulation and drying. Thus, a powder was prepared.

Example 2

| | |
|---|---|
| Taurine | 3000 mg |
| Thiamine nitrate | 5 mg |
| Riboflavin sodium phosphate | 5 mg |
| Pyridoxine hydrochloride | 5 mg |
| Sugar | 2000 mg |
| Maltitol | 3000 mg |
| Xylitol | 2500 mg |
| Acesulfame potassium | 19 mg |
| Citric acid | 1000 mg |
| Sodium citrate | appropriate amount |
| Flavor | small amount |
| Purified water | 100 ml in total |

Components listed above were mixed and dissolved in purified water. The pH was adjusted to 3.0 with sodium citrate, followed by sterilization at 95±5° C. Thus, a liquid preparation for internal administration was prepared.

Test Example 1

Forty subjects who were 20 years old or older and thought to have lifestyle diseases under the following conditions were grouped into 2 each consisting of 20 subjects. A placebo and the powder prepared in Example 1 were administered to the respective groups twice a day by 2.04 g (2000 mg in terms of taurine amount) in a single dose for 14 days. The change in the uric acid level was checked by a randomized double blind test.

Before this test was started, screening tests were conducted twice. Subjects who met all the conditions of Conditions 1 to 3 below in the first screening test were subjected to the second screening. Further, since the amount of taurine in the body seemed to influence the result of this test, subjects who met Condition 4 in addition to Conditions 1 to 3 in the second screening test were subjected to this test. In each administration group, the result was sub-grouped with a benchmark of the uric acid level of 7.0 mg/dL which served as the index for hyperuricemia. The uric acid levels were compared between the groups.

Table 1 below shows the result.

Incidentally, one case which was assigned to the taurine-administered group was terminated because another disease occurred before the administration was started.

Condition 1: LDL cholesterol was 140 mg/dL or above

Condition 2: triglyceride was 150 mg/dL or above but below 400 mg/dL

Condition 3: total cholesterol was 220 mg/dL or above

Condition 4: an amount of urinary taurine excreted (in urine collected for 24 hours) was 1500 μmol or below

TABLE 1

Unit: mg/dL

| Group | Uric acid level at start | Period evaluated | Number of cases | MEAN | S.D. | S.E. | MEDIAN | MIN | MAX | One-sample t-test | Test and estimation [two-sided, 95% confidence interval] Two-sample t-test | |
|---|---|---|---|---|---|---|---|---|---|---|---|---|
| Taurine-administered group | 7.0 mg/dL or above | at start | 8 | 8.11 | 0.72 | 0.25 | 8.30 | 7.0 | 9.1 | T = −7.128 P < 0.001 −0.75[−1.00 to −0.50] | T = −3.814 P = 0.001 −0.70[−1.09 to −0.31] | 7.0 mg/dL or above: taurine group vs placebo group T = −2.688 P = 0.020 −0.78[−1.42 to −0.15] |
| | | at completion | 8 | 7.36 | 0.67 | 0.24 | 7.50 | 6.4 | 8.3 | | | |
| | | degree changed | 8 | −0.75 | 0.30 | 0.11 | −0.70 | −1.3 | −0.3 | | | |
| | below 7.0 mg/dL | at start | 11 | 5.54 | 1.69 | 0.51 | 5.9 | 0.8 | 6.8 | T = −0.332 P = 0.747 −0.05[−0.35 | | |
| | | at completion | 11 | 5.49 | 1.53 | 0.46 | 5.9 | 1.1 | 6.5 | | | |

TABLE 1-continued

Unit: mg/dL

| Group | Uric acid level at start | Period evaluated | Number of cases | MEAN | S.D. | S.E. | MEDIAN | MIN | MAX | One-sample t-test | Two-sample t-test | Test and estimation [two-sided, 95% confidence interval] |
|---|---|---|---|---|---|---|---|---|---|---|---|---|
| | | degree changed | 11 | −0.05 | 0.45 | 0.14 | 0.1 | −0.9 | 0.5 | to 0.26] | | below 7.0 mg/dL: taurine group vs placebo group |
| Placebo-administered group | 7.0 mg/dL or above | at start | 6 | 7.83 | 1.01 | 0.41 | 7.50 | 7.0 | 9.8 | $T = 0.108$ | $T = -0.230$ | |
| | | at completion | 6 | 7.87 | 1.56 | 0.64 | 7.50 | 6.4 | 10.9 | $P = 0.918$ 0.03[−0.76 to 0.83] | $P = 0.821$ −0.05[−0.53 to 0.43] | $T = -0.883$ $P = 0.386$ |
| | | degree changed | 6 | 0.03 | 0.76 | 0.31 | 0.05 | −1.1 | 1.1 | | | |
| | below 7.0 mg/dL | at start | 14 | 5.86 | 0.68 | 0.18 | 5.90 | 4.1 | 6.8 | $T = 1.125$ | | −0.13[−0.44 to 0.18] |
| | | at completion | 14 | 5.95 | 0.88 | 0.24 | 5.85 | 3.8 | 7.3 | $P = 0.281$ 0.09[−0.08 to 0.25] | | |
| | | degree changed | 14 | 0.09 | 0.29 | 0.08 | 0.05 | −0.3 | 0.7 | | | |

From Table 1, the followings were observed among the subjects having a uric acid level of 7.0 mg/dL or above: the mean value and the median of the uric acid level in the placebo-administered group were increased by 0.03 mg/dL and 0.05 mg/dL, respectively; meanwhile, in the taurine-administered group, the mean value and the median were decreased by 0.75 mg/dL and 0.70 mg/dL, respectively. Moreover, a significant decrease (P<0.001) was observed in the uric acid level of the taurine-administered group when the administration was completed in comparison with when started; meanwhile, there was no significant difference in the uric acid level of the placebo-administered group between when the administration was started and when completed. Further, a significant difference (P=0.020) was observed between the taurine-administered group and the placebo-administered group.

Furthermore, the followings were observed among the subjects having a uric acid level of below 7.0 mg/dL in the taurine-administered group; the mean value of the uric acid level was decreased by 0.05 mg/dL, but the median was increased by 0.1 mg/dL. There was no significant difference in the uric acid level between when the administration was started and when completed. In comparison between the sub-groups having a uric acid level of 7.0 mg/dL or above and of below 7.0 mg/dL in the taurine-administered group, a significant difference (P=0.001) was observed between the sub-groups.

In addition, each administration group was sub-grouped with a benchmark of the uric acid level of 7.0 mg/dL at the start, and the percentage of change in the uric acid level was compared in each group. Table 2 below shows the result.

TABLE 2

( ): %

| Group | Uric acid level at start | Number of cases | subjects who showed decrease | subjects who did not show decrease |
|---|---|---|---|---|
| Taurine-administered group | 7.0 mg/dL or above | 8 | 8 (100.0) | 0 (0.0) |
| | below 7.0 mg/dL | 11 | 5 (45.5) | 6 (54.5) |
| Placebo-administered group | 7.0 mg/dL or above | 6 | 3 (50.0) | 3 (50.0) |
| | below 7.0 mg/dL | 14 | 4 (28.6) | 10 (71.4) |

From Table 2, among the subjects having a uric acid level of 7.0 mg/dL or above, the number of subjects who showed decrease in the uric acid level from the start was 3 (50.0%) in the placebo-administered group, while the number of subjects who did not show decrease (i.e., the uric acid level was increased or not changed) was 3 (50.0%). In contrast, all of 8 subjects in the taurine-administered group had the uric acid level decreased.

Test Example 2

The liquid preparation for internal administration prepared in Example 2 was administered once a day for 8 weeks to 121 subjects who were 20 years old or older and thought to have lifestyle diseases under the following conditions. Moreover, as in Test Example 1, the subjects were sub-grouped with a benchmark of the uric acid level of 7.0 mg/dL at the start. The uric acid levels were compared between the sub-groups.

Table 3 below shows the result.

Condition 1: serum triglyceride level was 150 mg/dL or above but below 400 mg/dL Condition 2: serum total cholesterol level was 200 mg/dL or above

TABLE 3

Unit: mg/dL

| Uric acid level at start | Period evaluated | Number of cases | MEAN | S.D. | S.E. | MEDIAN | MIN | MAX | One-sample t-test | Two-sample t-test |
|---|---|---|---|---|---|---|---|---|---|---|
| 7.0 mg/dL or above | at start | 48 | 7.96 | 0.84 | 0.12 | 7.75 | 7.0 | 10.8 | T = −5.922 | T = −3.936 |
| | at completion | 48 | 7.37 | 1.02 | 0.15 | 7.35 | 4.6 | 10.6 | P < 0.001 | P < 0.001 |
| | degree changed | 48 | −0.60 | 0.70 | 0.10 | −0.55 | −2.6 | 0.7 | −0.60[−0.80 to −0.39] | −0.46[−0.69 to −0.23] |
| below 7.0 mg/dL | at start | 73 | 5.64 | 0.89 | 0.10 | 5.6 | 3.3 | 6.9 | T = −2.060 | |
| | at completion | 73 | 5.50 | 1.03 | 0.12 | 5.3 | 2.8 | 7.6 | P = 0.043 | |
| | degree changed | 73 | −0.14 | 0.57 | 0.07 | −0.1 | −1.6 | 1.0 | −0.14[−0.27 to 0.00] | |

Test and estimation [two-sided, 95% confidence interval]

From Table 3, the followings were observed among the subjects having a uric acid level of 7.0 mg/dL or above: the mean value and the median were decreased by 0.60 mg/dL and 0.55 mg/dL, respectively; meanwhile, among the subjects having a uric acid level of below 7.0 mg/dL, the mean value and the median of the uric acid level were decreased by 0.14 mg/dL and 0.1 mg/dL, respectively. Thus, in both groups, the tendency that the uric acid level was decreased was observed. Nevertheless, in comparison between the sub-groups with the benchmark of the uric acid level of 7.0 mg/dL, a significant difference (P<0.001) was observed between the sub-groups.

In addition, the subjects were sub-grouped with the benchmark of the uric acid level of 7.0 mg/dL, and the percentage of change in the uric acid level was compared. Table 4 below shows the result.

TABLE 4

( ): %

| | | Change in uric acid level | |
|---|---|---|---|
| Uric acid level at start | Number of cases | subjects who showed decrease | subjects who did not show decrease |
| 7.0 mg/dL or above | 48 | 39 (81.3) | 9 (18.8) |
| below 7.0 mg/dL | 73 | 37 (50.7) | 36 (49.3) |

From Table 4, among the subjects having a uric acid level of 7.0 mg/dL or above, the number of subjects who showed decrease in the uric acid level from the start was 39 (81.3%), while the number of subjects who did not show decrease was 9 (18.8%). Meanwhile, among the subjects having a uric acid level of below 7.0 mg/dL, the number of subjects who showed decrease in the uric acid level from the start was 37 (50.7%), while the number of subjects who did not show decrease was 36 (49.3%).

Test Example 3

Sixteen subjects who were 20 years old or older and thought to have hyperuricemia under the following conditions were grouped into 2 each consisting of 8 subjects. A placebo and the powder prepared in Example 1 were administered to the respective groups twice a day by 2.04 g (2000 mg in terms of taurine amount) in a single dose for 14 days. The change in the uric acid level was checked by a randomized double blind test.

Before this test was started, screening tests were conducted twice. Subjects who met the condition of Condition below in the first screening test were subjected to the second screening. Subjects who met Condition again in the second screening test were subjected to this test. Furthermore, in this test, in order to check the change in a uric acid clearance value that would influence the change in the uric acid level, the uric acid level and the uric acid clearance value were measured four times, that is, 1 hour before administration, 1 hour after administration, 2 hours after administration, and 3 hours after administration when the taurine administration was started as well as similarly four times when the administration was completed. It should be noted that in order to make conditions equal between when the administration was started and when completed, the subjects were stayed in a hospital 3 days and 2 nights before each measurement, and had the same meals.

FIG. 1 shows the result.

Incidentally, one case which was assigned to the taurine-administered group was terminated because another disease occurred during the 14-day administration period.

Condition: serum uric acid level was 7.0 mg/dL or above but below 9.0 mg/dL

As shown in FIG. 1, in comparison between 1 hour before administration when the administration was started and 3 hours before administration when the administration was completed, it was observed that the mean value in the taurine-administered group was decreased by 0.53 mg/dL, but the decrease in the mean value in the placebo-administered group was only 0.18 mg/dL.

In addition, as in Test Examples 1 and 2, each administration group was sub-grouped with a benchmark of the uric acid level of 7.0 mg/dL at the start. The percentage of change in the uric acid level was compared in each group.

Table 5 below shows the result.

TABLE 5

| Group | Uric acid level at start | Number of cases | subjects who showed decrease | subjects who did not show decrease |
|---|---|---|---|---|
| | | | Change in uric acid level ( ): % | |
| Taurine-administered group | 7.0 mg/dL or above | 4 | 4 (100.0) | 0 (0.0) |
| | below 7.0 mg/dL | 3 | 2 (66.7) | 1 (33.3) |
| Placebo-administered group | 7.0 mg/dL or above | 5 | 3 (60.0) | 2 (40.0) |
| | below 7.0 mg/dL | 3 | 2 (66.7) | 1 (33.3) |

From Table 5, among the subjects having a uric acid level of 7.0 mg/dL or above, the number of subjects who showed decrease in the uric acid level from the start was 3 (60.0%) in the placebo-administered group, while the number of subjects who did not show decrease was 2 (40.0%). In contrast, all of 4 subjects in the taurine-administered group had the uric acid level decreased.

Next, the change (ratio of change) in the uric acid clearance value, when the administration was started, representing uric acid-excretion efficiency was compared between the administration groups.

Figure 2:
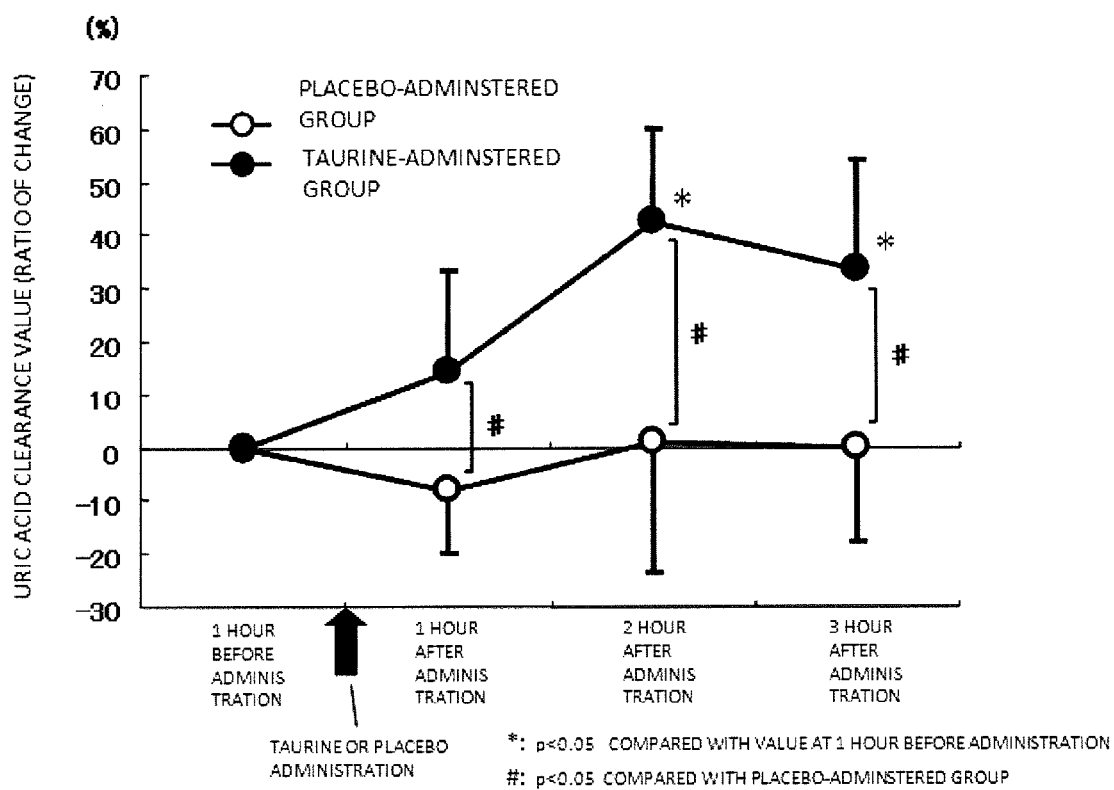
FIG. 2 is a graph illustrating changes in the uric acid clearance value (when the administration was started) of the taurine-administered group and the placebo-administered group.

FIG. 2 shows the result.

From FIG. 2, the followings were observed when the administration was started: in the taurine-administered group, the mean value of the ratio of change was increase by 40% or more at 2 hours after the administration and by 30% or more at 3 hours after the administration; nevertheless, in the placebo-administered group, change was hardly obtained. Moreover, between the administration groups, significant differences were obtained at each point of 1 hour, 2 hours, and 3 hours after the administration. Further, in the taurine-administered group, significant increases were observed at 2 hours and 3 hours after the administration in comparison with the value at 1 hour before the administration.

Moreover, the change (ratio of change) in the uric acid clearance value when the administration was completed was also compared between the administration groups.

Figure 3:
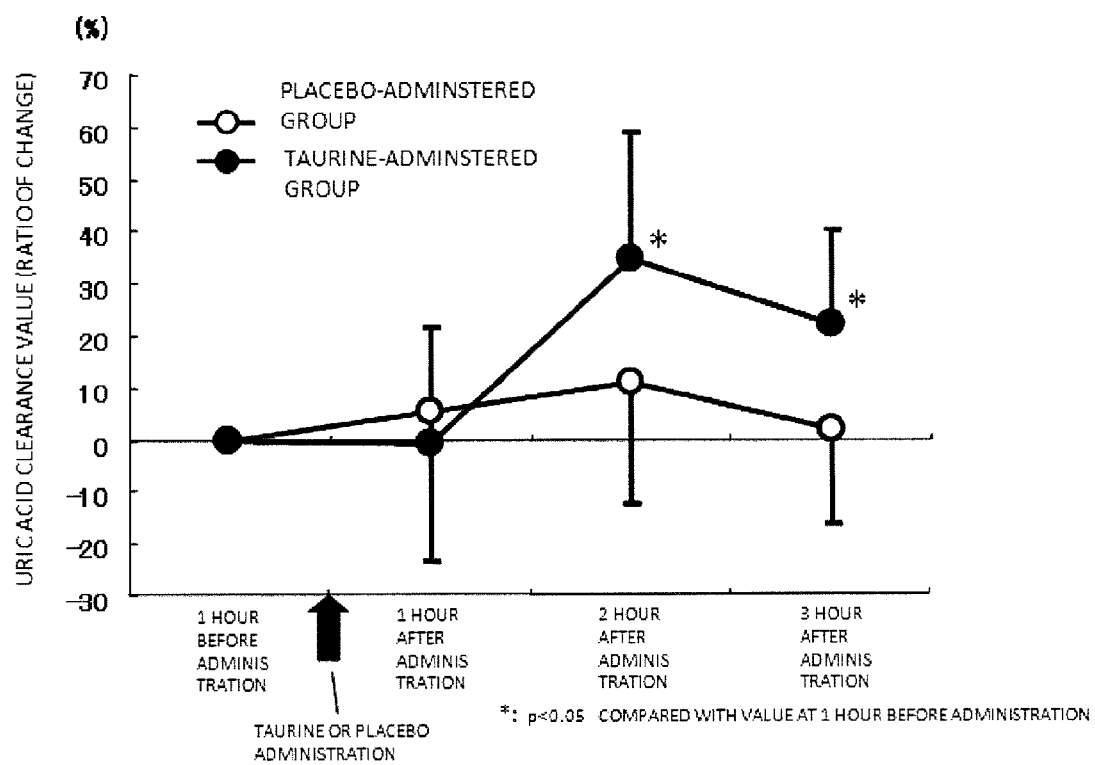
FIG. 3 is a graph illustrating changes in the uric acid clearance value (when the administration was completed) of the taurine-administered group and the placebo-administered group.

FIG. 3 shows the result.

From FIG. 3, the followings were observed when the administration was completed: in the taurine-administered group, the mean value of the ratio of change was increased by 30% or more at 2 hours after the administration and by 20% or more at 3 hours after the administration; nevertheless, in the placebo-administered group, merely approximately 10% increase was observed at 2 hours after the administration. Moreover, in the taurine-administered group, significant increases were observed at 2 hours and 3 hours after the administration in comparison with the value at 1 hour before the administration.

The change in the uric acid clearance value revealed that the effects of the present invention were caused by increase in the uric acid-excretion efficiency.

Next, degrees of serum uric acid levels changed before and after the administration in the taurine-administered cases of Test Examples 1 to 3 were lined up in the order of subjects having higher levels before the administration.

Figure 4:
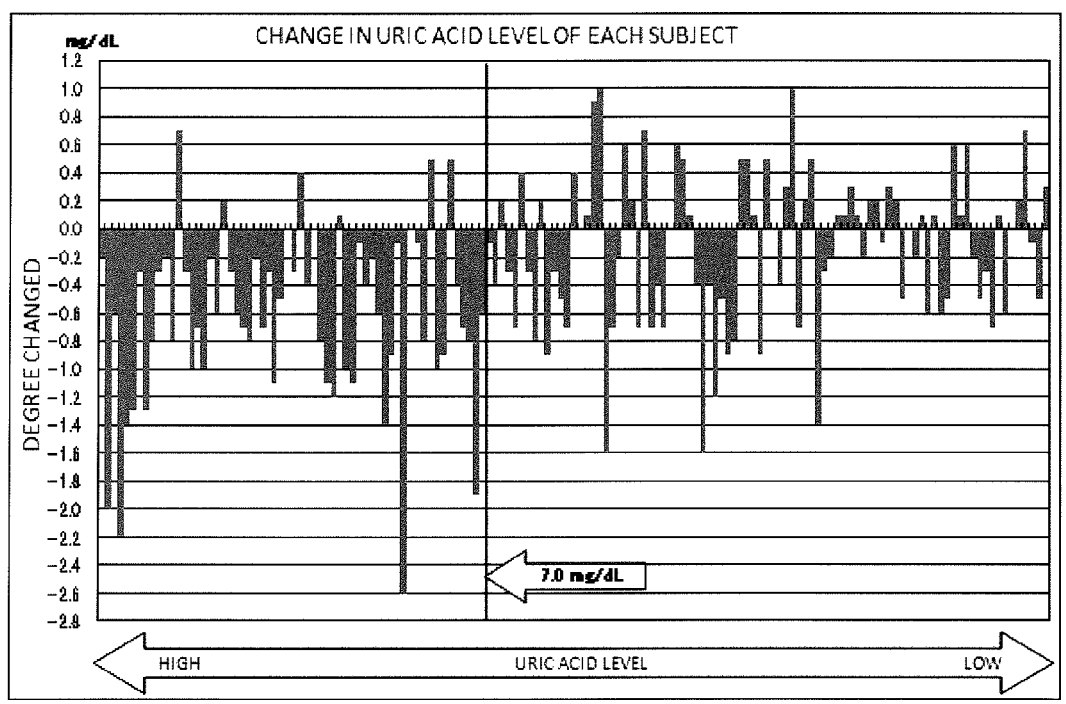
FIG. 4 is a graph illustrating the change in the serum uric acid level of each subject.

FIG. 4 shows the result.

Moreover, the taurine-administered cases of Test Examples 1 to 3 were summed and sub-grouped with a benchmark of the uric acid level of 7.0 mg/dL at the start. Degrees of uric acid levels changed were compared between the sub-groups.

Table 6 shows the result.

TABLE 6

Unit: mg/dL

| Uric acid level at start | Period evaluated | Number of cases | MEAN | S.D. | S.E. | MEDIAN | MIN | MAX | One-sample t-test | Two-sample t-test |
|---|---|---|---|---|---|---|---|---|---|---|
| | | | | | | | | | Test and estimation [two-sided, 95% confidence interval] | |
| 7.0 mg/dL or above | at start | 60 | 7.95 | 0.81 | 0.10 | 7.80 | 7.0 | 10.8 | T = −7.541 | T = −4.961 |
| | at completion | 60 | 7.33 | 0.96 | 0.12 | 7.35 | 4.6 | 10.6 | P < 0.001 | P < 0.001 |
| | degree changed | 60 | −0.62 | 0.64 | 0.08 | −0.60 | −2.6 | 0.7 | −0.62[−0.79 to −0.46] | −0.49[−0.69 to −0.30] |
| below 7.0 mg/dL | at start | 87 | 5.67 | 1.02 | 0.11 | 5.8 | 0.8 | 6.9 | T = −2.231 | |
| | at completion | 87 | 5.54 | 1.10 | 0.12 | 5.5 | 1.1 | 7.6 | P = 0.028 | |
| | degree changed | 87 | −0.13 | 0.55 | 0.06 | −0.1 | −1.6 | 1.0 | −0.13[−0.25 to −0.01] | |

From FIG. 4, the percentage of the uric acid level decreased was high in the subjects having a uric acid level of 7.0 mg/dL or above in comparison with the subjects having a uric acid level of below 7.0 mg/dL. Further, from Table 6, the followings were observed: in the subjects having a uric acid level of 7.0 mg/dL or above, the mean value and the median were decreased by 0.62 mg/dL and 0.60 mg/dL, respectively; meanwhile, in the subjects having a uric acid level of below 7.0 mg/dL, the mean value and the median of the uric acid level were decreased by 0.13 mg/dL and 0.1 mg/dL, respectively. Thus, in both groups, the tendency that the uric acid level was decreased was observed. Nevertheless, in comparison between the sub-groups with the benchmark of the uric acid level of 7.0 mg/dL, a significant difference (P<0.001) was observed between the sub-groups.

[Conclusion]

From the results of Test Examples 1 to 3 described above, a significant decrease in the uric acid level was observed after the oral administration of taurine. Further, it was observed that in subjects having a uric acid level of 7.0 mg/dL or above and diagnosed as hyperuricemia, the uric acid level was significantly lowered in comparison with subjects in a normal range. Accordingly, it was confirmed that taurine would be an active ingredient of anyone of preventive and therapeutic agents for hyperuricemia. This also suggested that taurine would be an active ingredient of any one of preventive and therapeutic agents for gout caused by a high uric acid level. Meanwhile, in subjects having a uric acid level of below 7.0 mg/dL, the percentage of the uric acid level decreased by taurine administration was low. Even when decrease in the uric acid level was observed, the decrease was so small. Suppose a case where the uric acid level of a hyperuricemia patient becomes a normal value by taurine administration and then taurine was further continuously administered thereto. Even in this case, conceivably the possibility that a problem is brought about is low, and the safety is also quite high.

INDUSTRIAL APPLICABILITY

The present invention makes it possible to provide a safe and highly effective composition for lowering a blood uric acid level, the composition comprising taurine as an active ingredient.

The invention claimed is:

1. A method of lowering a blood uric acid level, the method comprising administering taurine at a dose of 2000 mg to 4000 mg per day to a subject having a serum uric acid level of 7.0 mg/dL or above.

2. A method of treating hyperuricemia, the method comprising administering taurine in a dose of 2000 mg to 4000 mg per day to a subject having a serum uric acid level of 7.0 mg/dL or above.

3. A method of treating gout, the method comprising administering taurine in a dose of 2000 mg to 4000 mg per day to a subject having a serum uric acid level of 7.0 mg/dL or above.

* * * * *